(12) United States Patent
Kelly et al.

(10) Patent No.: US 7,732,574 B2
(45) Date of Patent: Jun. 8, 2010

(54) WOUND CARE PRODUCTS CONTAINING KERATIN

(75) Inventors: Robert James Kelly, Christchurch (NZ); Alisa Dawn Roddick-Lanzilotta, Lincoln (NZ); Mohammad Azam Ali, Lincoln (NZ)

(73) Assignee: Keraplast Technologies, Ltd., San Antonio, NY (US)

( * ) Notice: Subject to any disclaimer, the term of this patent is extended or adjusted under 35 U.S.C. 154(b) by 640 days.

(21) Appl. No.: 10/583,445

(22) PCT Filed: Dec. 16, 2004

(86) PCT No.: PCT/NZ2004/000323

§ 371 (c)(1),
(2), (4) Date: Apr. 27, 2007

(87) PCT Pub. No.: WO2005/058380

PCT Pub. Date: Jun. 30, 2005

(65) Prior Publication Data

US 2008/0038327 A1  Feb. 14, 2008

(30) Foreign Application Priority Data

Dec. 19, 2003  (NZ) .................................... 530296

(51) Int. Cl.
C08H 1/06 (2006.01)
A61L 15/00 (2006.01)
(52) U.S. Cl. .................................... 530/357; 424/445
(58) Field of Classification Search .................. None
See application file for complete search history.

(56) References Cited

U.S. PATENT DOCUMENTS

| | | | |
|---|---|---|---|
| 2,591,945 A | 4/1952 | Koerner et al. | |
| 3,567,363 A | 3/1971 | Wolfram | |
| 3,619,116 A | 11/1971 | Saville | |
| 3,644,084 A | 2/1972 | Hsiung et al. | |
| 3,883,647 A | 5/1975 | Geller | |
| 4,135,942 A | 1/1979 | Kikkawa | |
| 4,172,073 A | 10/1979 | Kadri et al. | |
| 4,407,793 A | 10/1983 | Akimova et al. | |
| 4,775,620 A | 10/1988 | Cardiff et al. | |
| 4,895,722 A | 1/1990 | Abe et al. | |
| 4,904,602 A | 2/1990 | Pigiet et al. | |
| 4,948,876 A | 8/1990 | Bore et al. | |
| 4,969,880 A | 11/1990 | Zamierowski | |
| 5,071,441 A | 12/1991 | Schnetzinger et al. | |
| 5,154,916 A | 10/1992 | Arraudeau et al. | |
| 5,358,935 A | 10/1994 | Smith et al. | |
| 5,460,967 A | 10/1995 | Fink et al. | |
| 5,602,094 A | 2/1997 | Goddard | |
| 5,763,583 A | 6/1998 | Arai et al. | |
| 5,830,481 A | 11/1998 | Cauwet-Martin et al. | |
| 5,932,552 A | 8/1999 | Blanchard et al. | 514/21 |
| 5,972,385 A | 10/1999 | Liu et al. | |
| 6,039,962 A | 3/2000 | Cauwet-Martin et al. | |
| 6,110,487 A | 8/2000 | Timmons et al. | |
| 6,124,265 A | 9/2000 | Timmons et al. | |
| 6,159,495 A | 12/2000 | Timmons et al. | |
| 6,203,574 B1 | 3/2001 | Kawamura | |
| 6,312,674 B1 | 11/2001 | Maubru et al. | |
| 6,432,435 B1 | 8/2002 | Timmons et al. | |
| 6,514,744 B2 | 2/2003 | Murata et al. | |
| 6,544,548 B1 | 4/2003 | Siller-Jackson et al. | |
| 6,783,546 B2 | 8/2004 | Zucherman et al. | |
| 6,846,940 B2 | 1/2005 | Gaetani et al. | |
| 7,169,896 B2 | 1/2007 | Schrooyen et al. | |
| 2001/0018614 A1 | 8/2001 | Bianchi | |
| 2002/0004068 A1 | 1/2002 | DiDrusco | |
| 2002/0013408 A1 | 1/2002 | Rhee et al. | |
| 2002/0035046 A1 | 3/2002 | Lukenbach et al. | |
| 2002/0183858 A1 | 12/2002 | Contiliano et al. | |
| 2003/0035820 A1 | 2/2003 | Timmons et al. | |
| 2003/0039676 A1 | 2/2003 | Boyce et al. | |
| 2006/0165635 A1 | 7/2006 | Kelly et al. | |
| 2006/0205652 A1 | 9/2006 | Zamora et al. | |

FOREIGN PATENT DOCUMENTS

| | | |
|---|---|---|
| CN | 1403643 | 3/2003 |
| CN | 1425813 | 6/2003 |
| EP | 0 628 573 A1 | 12/1994 |
| EP | 1 201 736 B1 | 4/2005 |
| FR | 1503640 | 12/1967 |
| FR | 2687577 A1 | 8/1993 |
| GB | 2 115 427 | 9/1983 |
| JP | 53-119900 | 10/1978 |
| JP | 54137064 | 10/1979 |
| JP | 63-301809 | 12/1988 |
| JP | 03-007596 | 1/1991 |

(Continued)

OTHER PUBLICATIONS

MacLaren, John A., et al., "Woods Science The Chemical Reactivity of the Wool Fibre", pp. 12-14, 1981.

(Continued)

Primary Examiner—Suzanne M. Noakes
(74) Attorney, Agent, or Firm—Vinson & Elkins LLP

(57) ABSTRACT

The invention relates to a would care product that provides a biochemical environment around a wound to promote wound healing. The wound care product includes a keratin protein fraction material in which the protein fraction is intact, is from the intermediate filament protein family or the high sulfur protein family and in which the protein fraction is S-sulfonated. The invention also described a method of making a wound care product.

10 Claims, 3 Drawing Sheets

FOREIGN PATENT DOCUMENTS

| | | |
|---|---|---|
| JP | 03-294297 | 12/1991 |
| JP | 05-222100 | 8/1993 |
| JP | 05-320358 | 12/1993 |
| JP | 06-100600 | 4/1994 |
| JP | 06-220713 | 8/1994 |
| JP | 06 192433 | 12/1994 |
| WO | WO 92/02238 | 2/1992 |
| WO | WO 98/51265 | 11/1998 |
| WO | WO 99/18922 | 4/1999 |
| WO | WO 99/19005 | 4/1999 |
| WO | WO 99/26570 | 6/1999 |
| WO | WO 00/23039 | 4/2000 |
| WO | WO 00/41739 | 7/2000 |
| WO | WO 00/70049 | 11/2000 |
| WO | WO 02/09659 | 2/2002 |
| WO | WO 03/011894 A1 | 2/2003 |
| WO | WO 03/018673 A1 | 3/2003 |
| WO | WO 03/103737 A1 | 12/2003 |

OTHER PUBLICATIONS

Hunter, Emma A.L., et al., "Cysteine and Methionin Supplementation Modulate the Effect of Tumor Necrosis Factor a on Protein Synthesis, Glutathione and Zinc Concentration of Liver and Lung in Rats Fed a Low Protein Diet", American Institute of Nutrition, vol. 124, No. 12, pp. 2319-2328, 1994.

Homandberg, G.A., et al., "Fibronectin Fragment Mediated Cartilage Chondrolysis. I. Suppression by Anti-Oxidants", Biochemica et Biophysica Acta, vol. 1317, pp. 134-142, 1996.

Parcell, Stephen, "Sulphur in Human Nutrition and Applications in Medicine", Alternative Medicine Review, vol. 7, No. 1, pp. 22-44, 2002.

Zafarullah, M., et al., "Molecular Mechanisms of N-Acetylcysteine Actions", Cellular and Molecular Life Sciences, vol. 60, No. 1, pp. 6-20, 2003.

Hummel, Klaus M., et al., "Cysteine Proteinase Cathepsin K mRNA Is Expressed in Synovium of Patients with Rheumatoid Arthritis and Is Detected at Sites of Synovial Bone Destruction", Journal of Rheumatology, vol. 25, No. 10, pp. 1887-1984, 1998.

Bradley, Helen, et al., "Sulfate Metabolism is Abnormal in Patients with Rheumatoid Arthiritis", Journal of Rheumatology, vol. 21, No. 7, pp. 1192-1196, 1994.

Wilkinson, L.J., et al., "Cysteine Diosygenase: Modulation of Expression in Human Cell Lines by Cytokines and Control of Sulphate Production", Toxicology in Vitro, vol. 16, pp. 481-483, 2002.

Tappaz, M.L., "Taurine Biosynthetic Enzymes and Taurine Transporter: Molecular Identification and Regulations", Neurochemical Research, vol. 29, No. 1, pp. 83-96, Jan. 2004.

Kontny, E., et al., "Impaired Generation of Taurine Chloramine by Synovial Fluid Neutrophils of Rheumatoid Arthritis Patients", Amino Acids, vol. 24, No. 4, pp. 415-418, 2002.

Roughley, Peter J., et al., "Cartilage Proteoglycans: Structure and Potential Functions", Microscopy Research and Technique, vol. 28, No. 5, pp. 385-397, 1994.

Rossi, Antonio, et al., "In Vitro Proteoglycan Sulfation Derived from Sulfhydryl Compounds in Sulfate Transporter Chondrodysplasias", Pediatric Pathology and Molecular Medicine, vol. 22, No. 4, pp. 311-321, 2003.

Kusche-Gullberg, Marion, et al., "Sulfotransferases in Glycosaminoglycan Biosynthesis", Current Opinion in Structural Biology, vol. 13, pp. 605-611, 2003.

Rath, Virginia L., "Sulfotransferase Structural Biology and Inhibitor Discovery", Drug Discovery Today, vol. 9, No. 23, pp. 1003-1011, Dec. 2004.

Venkatachalam, K.V., "Human 3'-phosphoadenosine 5'-phosphosulfate (PAPS) Synthase: Biochemistry, Molecular Biology and Genetic Deficiency", IUBMB Life, vol. 55, pp. 1-11, 2003.

Heyland, Daren K., et al., "Antioxidant Nutrients: A Systematic Review of Trace Elements and Vitamins in the Critically Ill Patient", Intensive Care Med., vol. 31, pp. 327-337, 2005.

Elsayed, Nabil M., "Antioxidant Mobilization in Response to Oxidative Stress: A Dynamic Environmental-Nutritional Interaction", Nutrition, vol. 17, pp. 828-834, 2001.

Serhan, Charles N., et al., "Resolution of Inflammation: The Beginning Programs the End", Nature Immunology, vol. 6, No. 12, pp. 1191-1197, Dec. 2005.

Henson, Peter M., "Dampening Inflammation", Nature Immunology, vol. 12, No. 12, pp. 1179-1182, Dec. 2005.

Verbruggen, G., "Chondroprotective Drugs in Degenerative Joint Diseases", Journal of Rheumatology, vo. 45, pp. 129-138, 2006.

Largo, R., et al., "Glucosomine Inhibits IL-1b-Induced NFkB Activation in Human Osteoarthritic Chondrocytes", OsteoArthritis and Cartilage, vol. 11, pp. 290-298, 2003.

Chan, P.S., et al., "Glucosamine and Chondroitin Sulfate Regulate Gene Expression and Synthesis of Nitric Oxide and Prostaglandin E2 in Articular Cartilage Explants", OsteArthritis and Cartilage, vol. 13, pp. 387-394, 2005.

Rassin, D.K., et al., "Nutritional Approaches to Improve Cognitive Development During Infancy: Antioxidant Compounds", Acta Paediatr Suppl., vol. 442, pp. 34-41, 2003.

Brugge, Karen L., et al., "The Role of Alterations in Free Radical Metabolism in Mediating Cognitive Impairments in Down's Syndrome", EXS, vol. 62, pp. 190-198, 1992.

Del Marmol, Veronique, et al., "Cysteine Deprivation Promotes Eumelanogenesis in Human Melanoma Cells", Journal of Investigative Dermatology, vol. 107, No. 5, pp. 698-702, 1996.

Smit, Nico P.M., et al., "Melanogenesis in Cultured Melanocytes Can Be Substantially Influenced by L-Tyrosine and L-Cysteine", Journal of Investigative Dermatology, vol. 109, No. 6, pp. 796-800, 1997.

Fujiwara, Y., et al., "Effect of Simultaneous Administration of Vitamin C, L-Cysteine and Vitamin E on the Melanogenesis", Biofactors, vol. 21, Nos. 104, pp. 415-418, 2004.

Kong, Kvvang-Noon, et al., "Expression and Characterization of Human Tyrosinase From a Bacterial Expression System", Comparative Biochemistry and Physiology, Part B, vol. 125, pp. 563-569, 2000.

Yamamura, Tatsuo, et al., "Antimelanogenic Activity of Hydrocoumarins in Cultured Normal Human Melanocytes by Stimulating Intracellular Glutathione Synthesis", Archives of Dermatological Research, vol. 294, No. 8, pp. 349-354m 2002.

Alonso, Laura C., et al., "Molecular Genetic and Endocrine Mechanisms of Hair Growth", Hormone Research, vol. 60, pp. 1-13, 2003.

Olney, J.W., et al., Brain Damage in Infant Mice Following Oral Intake of Glutamate, Aspartate or Cysteine, Nature, vol. 227, pp. 609-610, 1970.

Riise, G.C., "The Intrabronchial Microbial Flora in Chronic Bronchitis Patients: A Target for N-Acetylcysteine Therapy", European Respiratory Journal, vol. 7, pp. 94-101, 1994.

Grandjean, E.M., et al., "Efficacy of Oral Long-Term N-Acetylcysteine in Chronic Bronchopulmonary Disease: A Meta-Analysis of Published Double-Bline, Placebo-Controlled Clinical Trials", Clinical Therapy, vol. 22, pp. 209-221, 2000.

Hansen, N.C.G., et al., Orally Administered N-Acetylcysteine May Improve General Well-Being in Patients with Mild Chronic Bronchitis, Respitory Medicine, vol. 88, pp. 531-535, 1994.

Rasmussen, J.B., et al., Reduction in Days of Illness After Long-Term Treatment with N-Acetylcysteine Controlled-Release Tablets in Patients with Chronic Bronchitis, European Respitory Journal, vol. 1, pp. 351-355, 1988.

Parr, G.D., et al., Oral Fabrol (oral N-acetylcysteine) in Chronic Bronchitis, British Journal of Diseases of Chest, vol. 81, pp. 341-348, 1987.

Ardissino, D., et al., "Effect of Transdermal Nitroglycerin or N-acetylcysteine, or Both, in the Long-Term Treatment of Unstable Angina Pectoris", Journal of the American College of Caridiology, vol. 29, pp. 941-947, 1997.

Estensen, R.D., et al., "N-acetylcysteine Suppression of the Proliferative Index in the Colon of Patients with Previous Adenomatous Colonic Polyps", Cancer Letters, vol. 147, pp. 109-114, 1999.

Kinscherf, R., et al., Effect of glutathione Depletion and Oral N-acetylcysteine Treatment on CD4+ and CD8+ Cells. FASEB Journal, vol. 8, pp. 448-451, 1994.

Akerlund, et al., "Effect of N-acetylcystine (NAC) Treatment on HIV-1 Infection: A Double-Blind Placebo-Controlled Trial", European Journal of Clinical Pharmacology, vol. 50, pp. 457-461, 1996.
Zhang, Shumin, et al., "A Prospective Study of Plasma Total Cysteine and Risk of Breast Cancer", Epidemiology Biomarkers & Prevention, vol. 12, pp. 1188-1193, 2003.
James, L.P., et al., "Effect of N-Acetylcysteine on Acetaminophen Toxicity in Mice: Relationship to Reactive Nitrogen and Cytokine Formation", Toxicological Sciences, vol. 75, No. 2, pp. 458-467, 2003.
Shankar, K., et al., "Type 1 Diabetic Mice are Protected fro mAcetaminophen Hepatotoxicity", Toxicology Sciences, vol. 72, No. 2, pp. 220-234, 2003.
Goodman, M.T., Case-Control Study of Plasma Folate, Homocysteine, Vitamin B12, and Cysteine as Markers of Cervical Dysplasia, Cancer, vol. 89, No. 2, pp. 376-382, 2000.
Bernard, G.L. et al., "A Trial of Antioxidants N-Acetylcysteine and Procysteine in ARDS. The Antioxidant in ARDS Study Group", Chest, vol. 112, pp. 164-172, 1997.
Tepel, M., et al., "Prevention of Radiographic-Contrast-Agent-Induced Reductions in Renal Function by Acetylcysteine", New England Journal of Medicine, vol. 343, pp. 180-184, 2000.
Walters, M.T., et al., "A Double-Blind, Cross-Over, Study of Oral N-Acetylcysteine in Sjogren's Syndrome", Scand J. Rheumatol Suppl., vol. 61, pp. 253-258, 1986.
De Vries, N., et al., "N-acetyl-l-cysteine", Journal of Cellular Biochemistry Supplement, vol. 17F, pp. 270-277, 1993.
Beloqui, O., et al., "N-acetyl Cysteine Enhances the Response to Interferon-Alpha in Chronic Hepatitis C: A Pilot Study", Journal of Interferon Research, vol. 13, pp. 279-282, 1993.
Feghali, J.G., et al., "L-n-acetyl-cysteine Protection Against Cisplatin-Induced Auditory Neuronal and Hair cell Toxicity", Laryngoscope, vol. 111, No. 7, pp. 1147-1155, 2001.
Balli, R., "Controlled Trial on the Use of Oral Acetylcysteine in the Treatment of Glue-Ear Following Drainage", European Journal of Respitory Diseases, vol. 61, Suppl. 111, pp. 159, 1980.
Yalcin, E. et al., "N-acetylcysteine in Chronic Blepharitis", Cornea, vol. 21, pp. 164-168, 2002.
De Flora, S., et al., "Mechanisms fo N-acetylcysteine in the Prevention of DNA Damage and Cancer, with Special Reference to Smoking-Related End-Points", Carcinogenesis, vol. 22, pp. 999-1013, 2001.
Connors, S.L., et al., "Secretin and Autism: The Role of Cysteine", Journal of the American Academy of Child and Adolescent Psychiatry, vol. 38, pp. 795-796, 1999.
Apple, S.K., et al., "Effect of Feather Meal on Live Animal Performance and Carcass Quality and Composition of Growing Finishign Swing", Journal of Animal Science, vol. 81, pp. 172-181, 2003.
Loy, T.W., et al., "Effects of Supplementation on Intake an Growth of Nursing Calves Grazing Native Range in Southeastern North Dakota", Journal of Animal Science, vol. 80, pp. 2717-2725, 2002.
Pohl, Thomas, "Concentration of Proteins and Removal of Solutes", Methods in Enzymology, vol. 182, pp. 68-83, 1990.
McNeil, Steven, "Heavy Metal Removal Using Wool Filters", Asian Textile Journal, pp. 88-90, May-Jun. 2001.
Fukatsu, K., "Degradation of Fe(III)—Wool Keratin Complex by Hydrogen Peroxide", Kumanoto Women's University, Kumamoto, Japan, Sen'i Gakkaishi (Fiber), vol. 46, No. 5. pp. 186-191 1990.
Thomas, Helga, et al., "In Vitro Reconstitution of Wool Intermediate Filaments", Int. J. Biol. Macromol., vol. 8, pp. 258-264, Oct. 1986.
Harrap, B.S., et al., "Soluble Derivatives of Feather Keratin", Biochem J., vol. 92, No. 8, pp. 8-18, 1964.
Swan, J.M., "The Reaction of Protein Thiol and Disulphide Groups with Cupric Sulphite Solutions", pp. 69-83, Sep. 1960.
Mies, Von H.H., et al., "Preparative Gewinnung Ioslicher Proteine Aus Wolle", Das Leder, pp. 1-9, Jan. 1988.
Thomas, Helga, et al., "Experiments for the Isolation of Matrix Proteins of Wool in Disulphide Form", Melliand Textilberichte, pp. 297-300, Apr. 1983.
Goto M, Suyama K., "Occlusion of Transition Metal Ions by New Adsorbents Synthesized from Plant Polyphenois and Animal Fibrous Proteins", www.pubmed.gov, Dec. 18, 2006.

Mies, H.H., et al., "Chromatographic and Electrophoretic Investigation of the Properties of Unprotected Low-Sulphur Wool Kerateins", Journal of Chromatography, vol. 405, p. 365-370, 1987.
Pavlath, Attila E., et al., "Clarity of Films from Wool Keratin", Textile Res. J., vol. 69, No. 7, pp. 539-541, 1999.
Platt, A.J., et al., "A Comparative Study of Silicone Net Dressing and Paraffin Gauze Dressing in Skin-Grafted Sites", Burns, vol. 22, No. 7, pp. 543-545, 1996.
Valenta, Claudia, et al., "The Use of Polymers for Dermal and Transdermal Delivery", European Journal of Pharmaceutics and Biopharmaceutics, vol. 58, pp. 279-289, 2004.
Jonkman, Marcel F., et al., "New Method to Assess the Water Vapour Permeance of Wound Coverings", Biomaterials, vol. 9, pp. 263-267, May 1988.
Ming Yang, Jen, et al., "Properties of Chitosan Containing PP-g-AAa-g-NIPAAm Bigraft Nonwoven Fabric for Wound Dressing", Journal of Membrane Science, vol. 243, pp. 1-7, 2004.
Freedman, Gordon, et al., "Practical Treatment of Pain in Patients with Chronic Wounds: Pathogenesis-Guided Management", The American Journal of Surgery, vol. 188, pp. 31S-35S, 2004.
Coderch, L., et al., "Chromatographic Characterization of Internal Polar Lipids from Wool", JAOCS, vol. 72, No. 6, pp. 715-720, 1995.
Coderch, L., et al., "Physicochemical Characteristics of Liposomes Formed with Internal Wool Lipids", JAOCS, vol. 73, No. 12, pp. 1713-1718, 1996.
Wertz, Philip W., et al., "The Composition of the Ceremides from Human Stratum Corneum and from Comedones", The Journal of Investigative Dermatology, vol. 84, No. 5, pp. 410-412, 1985.
Matsumoto, Kiyoichi, et al., "Studies on Regenerated Protein Fibers, III. Production of Regenerated Silk Fibroin Fiber by the Self-Dialyzing Wet Spinning Method", Journal of Applied Polymer Science, vol. 60, pp. 503-511, 1996.
Yang, Yiqi, et al., "Formaldehyde-Free Zein Fiber-Preparation and Investigation", Journal of Applied Polymer Science, vol. 59, pp. 433-441, 1996.
Cates, David M., et al., "Preparation and Properties of Fibers Containing Mixed Polymers III. Polyacrylonitrile-Silk Fibers", Journal of Polymer Science, vol. 21, No. 97, pp. 125-138, 1956.
Schimpf, Warren C., "Fibers from Regenerated Collagen", Ind. Eng. Chem., Prod. Res. Dev., vol. 16, No. 1, pp. 90-92, 1977.
Sastry, T.P., et al., "Graft Copolymerization of Feather Keratin Hydrolyzate: Preparation and Characterization", Journal of Polymer Materials, vol. 14, No. 2, pp. 177-181, 1997.
Tanabe, Toshizumi, et al., "Preparation and Characterization of Keratin-Chitosan Composition Film", Biomaterials, vol. 23, pp. 817-825, 2002.
Yamauchi, Kiyoshi, et al., "Cultivation of Fibroblast Cells on Keratin-Coated Substrata", J. Biomater Sci. Polymer Edn., vol. 9, No. 3, pp. 259-270, 1998.
Braverman, E.R., et al., "The Healing Nutrients Within: Facts, Findings, and New Research on Amino Acids", Basic Health Publications, Inc. 2003.
Gillespie, J. Morton, "The Structural Proteins of Hair: Isolation, Characterization, and Regulation of Biosynthesis", Biochemistry and Physiology of the Skin, pp. 475-510, 1983.
Marshall, R.C., et al., "Structure and Biochemistry of Mammalian Hard Keratin", Electron Microsc. Rev., vol. 4, pp. 47-83, 1991.
Gillespie, J.M., et al., "Variability in the Proteins of Wool and Hair", Division of Protein Chemistry, CSIRO, vol. 2, pp. 67-77, 1980.
Milgrim, Norton W., et al., "Landmark Discrimination Learning in the Dog: Effects of Age, an Antioxidant Fortified Food, and Cognitive Strategy", Neuroscience and Biobehavioral Reviews, vol. 26, pp. 679-695, 2002.
Kazunori, Katoh, et al., "Preparation and Properties of Keratin-Poly(vinyl alcohol) Blend Fiber", Journal of Applied Polymer Science, vol. 91, pp. 756-762, 2004.
Encyclopedia of Polymer Science and Technology—Plastics, Resins, Rubbers, Fibers, vol. 8,, pp. 338-341.
Gorman, Jessica, "Materials Take Wing: What to Do With 4 Billion Pounds of Feathers?", Science News, vol. 161, p. 120(2), Feb. 23, 2002.

WOUND CARE PRODUCTS CONTAINING KERATIN

FIELD

The invention relates to wound care products containing keratin.

BACKGROUND OF THE INVENTION

Wounds and lesions can be caused by a variety of events, including surgery, traumatic injury, burns, abrasions and skin grafts. Healing of wounds may be difficult and may result in problems such as ulcers and septicemia. Of particular concern are chronic wounds, such as pressure sores and diabetic ulcers. The treatment of these conditions is of increasing importance as the population ages. The conventional cascade of biochemical processes which occurs in wound healing, involving hemostasis and inflammation, granulation tissue formation and reepithelization and remodeling, is disrupted in the case of chronic wounds due in part to the prolonged inflammatory response which occurs, and the release of destructive enzymes by inflammatory cells.

It has been recognized for some time that maintaining a moist environment can improve the rate of wound healing. Many products have been developed which provide this environment in order to increase the rate of repair of chronic wounds. The materials used in these dressings are biocompatible to some extent, and include polylactic acid, chitin, alginate derivatives and collagen. The response of these materials to wound exudates, and the biochemical environment that these materials provide are fundamental to their performance in the wound.

Commercially available dressings include various synthetic materials such as silicone compounds, nylon fabrics, or petrolatum gauzes and the like [A. J. Platt, A. Phipps and K. Judkins, A comparative study of silicone net dressing and paraffin gauze dressing in skin-grafted sites, Burns, 22(7), 1996, p. 543-545; Claudia Valenta and Barbara G. Auner, The use of polymers for dermal and transdermal delivery, European Journal of Pharmaceutics and Biopharmaceutics, 58(2), 2004, p. 279-289]. Whilst these conventional wound dressing materials are inexpensive and easily available, they generally have poor affinity with the wounded area, insufficient vapour permeability are ultimately unsatisfactory with regards to long term healing of chronic wounds [Marcel F. Jonkman, Izaäk Molenaar, Paul Nieuwenhuis, Peter Bruin and Albert J. Pennings, New method to assess the water vapour permeance of wound coverings, Biomaterials, 9(3), 1988, p. 263-267]. High-performance wound dressing materials are often derived from natural materials having properties similar to those of the patients' skin.

Wound dressing can be created using natural materials or through combination of synthetic materials and natural materials (JP# 47470/1988; Jen Ming Yang and Hao Tzu Lin, Properties of chitosan containing PP-g-AA-g-NIPAAm bigraft nonwoven fabric for wound dressing, Journal of Membrane Science, 243(1-2), 2004, p. 1-7). The use of wound dressings is an extremely important part of wound management and vital to achieve successful healing outcomes [Gordon Freedman, Hyacinth Entero and Harold Brem, Practical treatment of pain in patients with chronic wounds: pathogenesis-guided management, The American Journal of Surgery, 188(1), 2004, p. 31-35]. An optimum wound dressing protects the injured tissue, maintains a moist environment, is water permeable, maintains microbial control, delivers healing agents to the wound site, is easy to apply, does not require frequent changes and is non-toxic and non-antigenic.

Currently several forms of wound dressings materials are available commercially, including occlusive dressings, non-adherent dressings, absorbent dressings, and dressings in the form of sheets, foams, powders and gels. Attempts have been made to provide improved dressings, particularly for chronic wounds, that assist in the wound healing process by using biological materials such as cells and growth factors. To date, these biologicals have proven very costly due to factors such as manufacturing processes and storage and stability issues, and in addition they have shown minimal clinical relevance in accelerating the chronic wound healing process. Above all effective, wound management requires an understanding of the process of tissue repair and knowledge of the properties of the wound dressing materials. Only when these two factors are considered together can the process of dressing selection be undertaken in a rational and informed fashion.

Keratin proteins are present in a wide range of biological tissue, performing a structural role in skin, hair and other materials. Keratins extracted from hair have been shown to be a valuable component in wound dressings. U.S. Pat. No. 5,932,552 provides a biocompatible keratin material prepared by either reduction or oxidation for use as a component in wound care products. Those methods included in the art for the oxidation of keratins to create a polar group are harsh and degrading to the keratin, causing protein damage and loss of core physical characteristics arising from the protein amino acid composition and tertiary structure. In addition the oxidation processes used in the preparation of these materials are irreversible and the cysteic acid groups formed cannot be reconverted to cystine to perform a useful structural function. Those methods included in the art for reduction to create soluble proteins are conducted under harsh alkaline conditions that also cause damage to the protein and loss of the core physical characteristics of the keratin proteins.

The core components of keratin fibres, specifically the intermediate filament proteins and the matrix proteins present in wool and hair, play particular roles within the fibre which is reflected in their tertiary structure and amino acid composition. These same features can be capitalized upon to create materials with good physical properties and highly absorbing capacities when using purified forms of these proteins. In order to do this, methods used for isolating keratins need to be mild, to prevent protein damage, create cystine modifications that are reversible, to allow for reconstitution of tough materials through the creation of cystine bonds, and facilitate the isolation of specific keratin protein fractions from the keratin source. The present invention provides new materials for use in wound care products that are prepared according to these principles.

OBJECT OF THE INVENTION

It is an object of the invention to provide a wound care product which uses a keratin protein fraction. It is a further object of the invention to provide a keratin protein fraction that is intact and S-sulfonated for use in wound care, or to at least provide the public with a useful choice.

SUMMARY OF THE INVENTION

The invention provides a material for treating a wound comprising a keratin protein fraction in which the protein fraction is intact.

The invention also provides a material for treating a wound comprising a keratin protein fraction in which the protein fraction is from the intermediate filament protein family.

The invention also provides a material for treating a wound comprising a keratin protein fraction in which the protein fraction is from the high sulphur protein family.

The invention also provides a material for treating a wound comprising a keratin protein fraction in which the protein fraction is s-sulfonated.

The protein fraction may be hydrolysed.

The protein is preferably s-sulfonated.

The protein may be from the high sulphur protein family.

The protein may be an intermediate filament protein.

The material is preferably a fibre, a film, a foam or a hydrogel.

The invention also provides a method a method for making a wound care product comprising
 a) preparing a 10% solution of a keratin protein;
 b) mixing the keratin protein and a water soluble polymer to form an intimate mixture;
 c) casting the aqueous mixture so produced; and
 d) freezing and thawing in sequence to produce a hydrogel.

The physico-mechanical properties of the biomaterials may be improved by introducing cross-linker agents to form disulfide bonds and thus remove sulfonate functionalities.

The cross-linking agent used as a reductant may be a thiol or thioglycollate salt.

The physico-mechanical properties may be wet and dry strength.

The thioglycollate salt may be ammonium thioglycollate solution.

The water soluble polymer may be polyvinyl alcohol, polyvinylpyrolidone, polyethylene glycol or the like.

The invention also provides a method of improving the wet strength properties of the wound care products produced by the method of the invention by incorporating a cross-linking agent into them.

The cross-linking agent is preferably an aldehyde.

The cross-linking agent may be selected form the group consisting of formaldehyde, glyoxal, glutaraldehyde and the like.

BRIEF DESCRIPTION OF THE DRAWINGS

The invention will now be described, by way of example only, with reference to the following specific embodiments.

DETAILED DESCRIPTION OF THE INVENTION

Figure 1:
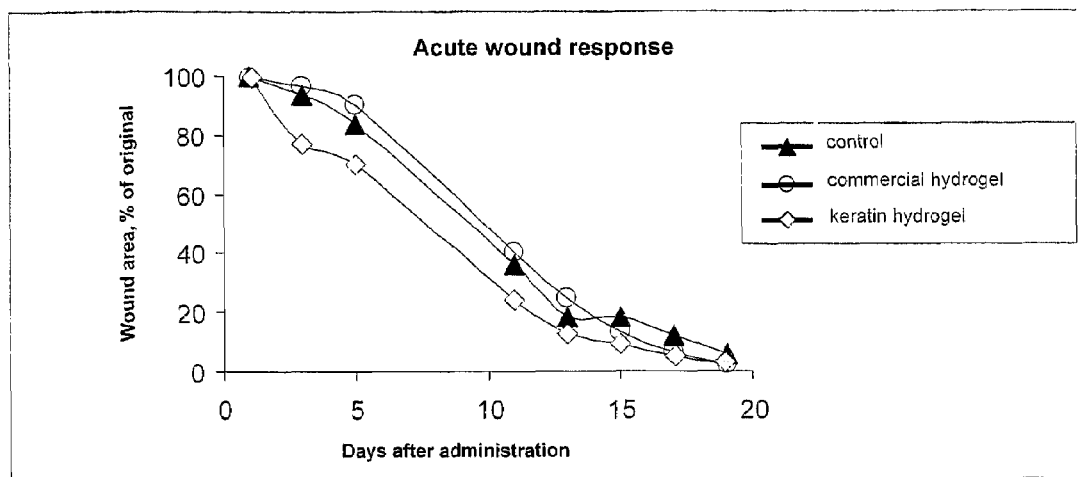
FIG. 1: shows the response of wounds treated with keratin and other materials

The hard alpha keratin proteins such as those derived from human hair, wool, animal fibres, horns, hooves or other mammalian sources, can be classified into particular components according to their biochemical properties, specifically their molecular weight and amino acid composition. Table 1 illustrates the amino acid composition determined by conventional analytical methods of typical keratin protein fractions known in the art and also the subject of this invention. This involves acid hydrolysis of the analyte which converts all cystine and labile cystine derivatives to cysteine, typically recorded as half-cystine.

TABLE 1 amino acid composition of keratin fractions: S-sulfonated keratin intermediate filament protein (SIFP), S-sulfonated keratin high sulfur protein (SHSP), S-sulfonated keratin peptide (SPEP) as used in the invention. Intermediate filament protein (IFP), high sulfur protein (HSP) and whole wool courtesy of Gillespie and Marshall, Variability in the proteins of wool and hair, Proc. Sixth Int. Wool Text. Res. Conf., Pretoria, 2, 67-77, 1980. All residues expressed as mol %. S-sulfocysteine, cystine and cysteine are measured as S-carboxymethyl cysteine following reduction and alkylation, and reported as cys.

|     | SIFP | SHSP | SPEP | IFP  | HSP  | Whole wool |
|-----|------|------|------|------|------|------------|
| Cya | 0.4  | 1.7  | 0.7  | 0    | 0    | 0          |
| Asp | 7.9  | 2.6  | 8    | 9.6  | 2.3  | 5.9        |
| Glu | 15.4 | 8.6  | 15   | 16.9 | 7.9  | 11.1       |
| Ser | 10.9 | 14.3 | 11.4 | 8.1  | 13.2 | 10.8       |
| Gly | 8.1  | 9.1  | 8.4  | 5.2  | 6.2  | 8.6        |
| His | 0.9  | 0.8  | 0.9  | 0.6  | 0.7  | 0.8        |
| Arg | 7.9  | 6.8  | 6.9  | 7.9  | 6.2  | 6.2        |
| Thr | 6.5  | 10.4 | 6.5  | 4.8  | 10.2 | 6.5        |
| Ala | 7.5  | 3.6  | 7.5  | 7.7  | 2.9  | 5.2        |
| Pro | 5.4  | 12.6 | 5.7  | 3.3  | 12.6 | 6.6        |
| Tyr | 1.1  | 1.8  | 1.2  | 2.7  | 2.1  | 3.8        |
| Val | 6.5  | 6.3  | 5.8  | 6.4  | 5.3  | 5.7        |
| Met | 0.2  | 0    | 0.3  | 0.6  | 0    | 0.5        |
| Lan | 0.2  | 0.2  | 0.3  | 0    | 0    | 0          |
| Ile | 3.7  | 2.9  | 3.4  | 3.8  | 2.6  | 3          |
| Leu | 8.9  | 3.9  | 8    | 10.2 | 3.4  | 7.2        |
| Phe | 2.5  | 1.5  | 2.1  | 2    | 1.6  | 2.5        |
| Lys | 2.1  | 0.4  | 2.1  | 4.1  | 0.6  | 2.7        |
| Cys | 4.2  | 12.4 | 4.6  | 6    | 22.1 | 13.1       |

Table 2 illustrates the molecular weight determined by conventional analytical methods of typical keratin protein fractions known in the art and also the subject of this invention. Conventional analysis involves cleavage of cystine bonds within the keratin using reduction so that the protein mass is determined in its native, uncrosslinked state, most similar to the unkeratinised state of the protein. Mass is determined using polyacrylamide gel electrophoresis. In the case of the peptide SPEP mass is determined using mass spectrometry. Using these methods the keratin is made soluble without any hydrolysis of peptide bonds and an accurate measure of molecular weight is determined.

TABLE 2

Molecular weight of keratin fractions: S-sulfonated keratin intermediate filament protein (SIFP), S-sulfonated keratin high sulfur protein (SHSP), S-sulfonated keratin peptide (SPEP) as used in the invention. Intermediate filament protein (IFP) and high sulfur protein (HSP) courtesy of Gillespie and Marshall, Variability in the proteins of wool and hair, Proc. Sixth Int. Wool Text. Res. Conf., Pretoria, 2, 67-77, 1980.

| Keratin protein fraction | Molecular weight/kD |
|--------------------------|---------------------|
| SIFP                     | 45-60               |
| SHSP                     | 10-25               |
| SPEP                     | <1                  |
| IFP                      | 45-60               |
| HSP                      | 11-23               |

Both amino acid composition and molecular weight varies, to a small extent, across keratin types, between species and also within breeds of one species, for example between wools from different breeds of sheep. The figures given in Tables 1 and 2 are indicative for the keratin source stated. However, individual types of keratin proteins, or keratin protein fractions, have distinctive characteristics, particularly molecular weight and amino acid content.

The subject of the invention is materials containing intact S-sulfonated keratin protein fractions. "Intact" refers to proteins that have not been significantly hydrolysed, with hydrolysis being defined as the cleavage of bonds through the addition of water. Gillespie (Biochemistry and physiology of the skin, vol 1, Ed. Goldsmith Oxford University Press, London, 1983, pp 475-510) considers "intact" to refer to proteins in the keratinized polymeric state and further refers to polypeptide subunits which complex to form intact keratins in wool and hair. For the purpose of this invention "intact" refers to the polypeptide subunits described by Gillespie. These are equivalent to the keratin proteins in their native form without the disulfide crosslinks formed through the process of keratinisation.

Keratin protein fractions are distinct groups from within the keratin protein family, such as the intermediate filament proteins, the high sulfur proteins or the high glycine-tyrosine proteins well known in the art. Intermediate filament proteins are described in detail by Orwin et al (*Structure and Biochemistry of Mammalian Hard Keratin*, Electron Microscopy Reviews, 4, 47, 1991) and also referred to as low sulphur proteins by Gilliespie (Biochemistry and physiology of the skin, vol 1, Ed. Goldsmith Oxford University Press, London, 1983, pp 475-510). Key characteristics of this protein family are molecular weight in the range 40-60 kD and a cysteine content (measured as half cystine) of around 4%. The high sulfur protein family are also well described by Orwin and Gillispie in the same publications. This protein family has a large degree of heterogeity but can be characterised as having a molecular weight in the range 10-30 kD and a cysteine content of greater than 10%. The subset of this family, the ultra high sulfur proteins can have a cysteine content of up to 34%. The high glycine-tyrosine protein family are also well described by Orwin and Gillespie in the same publications. This family is also referred to as the high tyrosine proteins and has characteristics of a molecular weight less than 10 kD, a tyrosine content typically greater than 10% and a glycine content typically greater than 20%.

For the purpose of this invention a "keratin protein fraction" is a purified form of keratin that contains predominantly, although not entirely, one distinct protein group as described above. In the context of this invention S-Sulfonated keratins have cysteine/cystine present predominantly in the form S-sulfocysteine, commonly known as the Bunte salt. This highly polar group imparts a degree of solubility to proteins. Whilst being stable in solution, the S-sulfo group is a labile cysteine derivative, highly reactive towards thiols, such as cysteine, and other reducing agents. Reaction with reducing agents leads to conversion of the S-sulfo cysteine group back to cysteine. S-sulfo cysteine is chemically different to cysteic acid, although both groups contain the $SO_3^-$ group. Cysteic acid is produced irreversibly by the oxidation of cysteine or cystine and once formed cannot form disulfide crosslinks back to cysteine. S-sulfocysteine is reactive towards cysteine and readily forms disulfide crosslinks.

SIFP can be prepared by methods such as those described in WO03011894.

The aspect and other details of the invention will now be more particularly described.

Highly S-sulfonated keratins have been shown to be able to be formed into a variety of matrices including porous sponges, films and fibres using methods such as those outlined in NZ/PCT/00169 (which is incorporated herein).

Purified wool keratin intermediate filament proteins are particularly well suited to reformation into matrices, due in part to their high molecular weight and their tertiary structure. Methods outlined in NZ/PCT/00169 make extensive use of these materials to form useful matrices.

S-sulfo keratins can be prepared by a variety of methods, including those outlined in PCT/NZ02/00125 (which is incorporated herein).

Porous sponge matrices are of particular use in a wound environment as they can play an important role in absorbing wound exudates and maintaining a healthy environment for healing a wound. In addition they can act as media for the delivery of other healing agents, such as growth factors, antibacterial agents or cultured cells, that stimulate the healing process. These features are enhanced through using S-sulfonated keratin protein fractions to construct the matrices. The highly polar nature of the S-sulfo group makes matrices derived from this material highly absorbing. In addition, S-sulfonated keratins are biocompatible and do not invoke an adverse response in vitro.

Films are an important component in dressings for the treatment of wounds, providing a barrier to protect the wound and maintaining an appropriate environment to encourage healing. S-sulfonated keratins films are biocompatible and do not invoke an adverse response in vitro. As such, they are useful components in a wound dressing.

Fibres reconstituted from S-sulfonated keratin intermediate filament proteins can be used as a component for wound dressings. Fibres are particularly versatile as they can be formed into woven or non-woven constructs and fibre design can be used as well control of the chemistry of the material to effect the interaction of the dressing with the wound. Much work has been undertaken into the use of regenerated fibres in wound care, in particular alginate fibres. Reconstituted keratin fibres derived from S-sulfonated intermediate filament proteins are a new material for use in similar applications.

Hydrogels are frequently used in wound dressings and play an in important role in controlling the wound environment and provide a suitable medium for the delivery of actives to stimulate or assist healing. S-sulfonated keratins, in particular S-sulfonated intact keratin intermediate filament protein, is an excellent substrate for the formation of hydrogels as a result of the high degree of order and intermolecular interaction achievable as a result of the intact nature of the proteins.

Keratin materials derived from the SIFP and SHSP protein fractions contain differing amounts of the highly polar S-sulfo group, and consequently differ in their physicochemical characteristics, in particular their ability to absorb moisture. Wound dressings derived from a combination of these absorb moisture to a greater or lesser extent, and so can be controlled in the degree to which they will absorb wound exudates.

S-sulfonated keratin proteins prepared as spray or freeze dried powders are highly absorbing materials that are a valuable component in wound dressings, in particular for use in the hydrogel type dressing in which alginates or collagen derivatives are the materials used frequently in currently available products. Combination of the SIFP and SHSP proteins leads to a degree of control over the absorbing capacity of the powder and the nature of the gel formed on absorbance, due to the variation in the amount of S-sulfo groups present within each protein fraction.

Due to the intact nature of the proteins, and the water solubility of the material arising from the presence of the polar S-sulfonate group, S-sulfonated keratin protein fractions, in particular the keratin intermediate filament protein fraction, can be readily formed into a variety of matrices and the physical properties of these matrices are such that they can provide a useful physical role in a wound environment. Furthermore, the materials can be chemically treated following reformation into films, fibres or sponges, to remove the S-sulfonate functionality and generate disulfide crosslinks within the material, similar to those present in the native keratin. Methods for this treatment are described in NZ/PCT/00169. When treated in this way, the keratin matrices are less absorbing and retain their structure in a wound environment. They are well suited to the delivery of bioactives to the wound site, such as antibacterial agents, growth factors, antibiotic treatments, cultured cells or other drugs.

The physical and mechanical properties of the wound dressing or healing membranes can be readily improved through a variety of methods. One method involves treatment with a reducing reagent such as ammonium thioglycolate solution at pH=7.0 for 1 hour in order to remove the sulfonate functionality from S-sulfonate keratin and introduce cystine disulfides as crosslinks. This causes significant improvement in the mechanical properties particularly wet strength of the membranes materials. Chemical conversion is confirmed using Fourier-Transform Infra-Red (FT-IR) spectroscopic studies as the S-sulfonated group gives rise to a strong and sharp absorbance at 1022 $cm^{-1}$ which is observed to disappear on exposure of the S-sulfonated to the reagents described.

A method for the improvement of the physical and mechanical strength of keratin hydrogel biomaterials is to increase the hydrogen bonding network between the keratin protein chains or the keratin protein and other polymers, such as polyvinyl alcohol and polyvinyl pyrolidone. This can be achieved by using a freezing-thawing process during the constructing hydrogel sheets. This is confirmed by an increase in the insolubility of hydrogels formed using this process.

Production of a chemically cross-linked hydrogel biomaterial is another embodiment in the invention. Improving physical properties such as insolubility and strength in swollen states can be achieved by using chemical cross-linkers such as glutaraldehyde, that allow the formation of chemical cross-links between keratin protein chains.

Further, the physical properties of the keratin based membranes and hydrogels can be increased by standard protein cross-linking methods including using, typical chemical cross-linkers such as, glutaraldehyde, formaldehyde, carbodiimides, e.g., 1-ethyl-3-(dimethylaminopropyl)carbodiimide, 2,5-hexanedione, diimidates, e.g., dimethylsuberimidate, or bisacrylamides, e.g., N,N'-methylenebisacrylamide.

In vitro Testing

The biological response for the materials described above has been determined in vitro through growth of cells relevant in wound healing, and immunogenic response, specifically fibroblasts and lymphocytes.

TABLE 3

Keratin materials tested in vitro.

| Keratin material | Cystine functionality | Label |
|---|---|---|
| Sponge | S-sulfonate | A |
| Sponge | disulfide | B |
| Film | S-sulfonate | C |
| Film | disfulfide | D |
| Powder | S-sulfonate | E |

Figure 2:
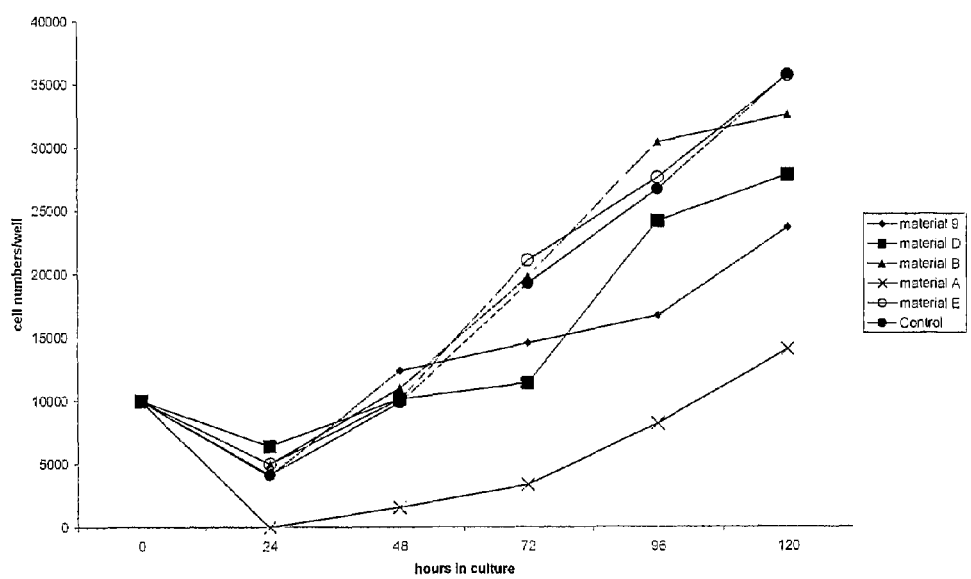
FIG. 2: shows sheep fibroblast proliferation on keratin materials.

Sheep Fibroblasts:

FIG. 2 is a graph showing the effect of different keratin matrices on ovine dermal fibroblast cell proliferation relative to cell media alone (control). Parallel samples of n=3 were used for each time point.

The proliferation kinetics of ovine fibroblasts on most of the keratin matrices is similar. Wells are initially seeded with ~10,000 cells (0 hours). During the first 24 h post-seeding, the culture experiences a lag time as evidenced by the decline hi cell numbers. This phenomenon has been recognised in all assays performed and the drop is observed in control wells in addition to those containing the test materials. Additional shorter time-course experimentation has shown that this lag time lasts for less than 12 h (data not shown) and that the exponential phase of growth begins at this point. Population doublings occur approximately every 24 h-48 h with subconfluency (approximately 80% confluency) marking the end of logarithmic growth. This corresponds to the end of the experimental time course (5 days or 120 h). Extended time-course experiments have indicated a plateau in cell growth shortly after this with full confluence of the culture. Contact inhibition and depletion of nutrients play a key role in limiting the growth rate at this point and the monolayer culture exhibits signs of cell death (i.e. loss of membrane integrity, reduction in cell numbers, vacuolisation of individual cells).

Such kinetics are exhibited by sheep fibroblasts on most of the biopolymer substrates, particularly the films and sponge samples.

With respect to the individual matrix types, the following observations were made:

Films. The films with the disulfide chemical configuration support sheep fibroblast growth most satisfactorily (material D). A second sodium S-sulfonate salt configuration demonstrated by film material C supports cell growth to a lesser degree and tends to swell in culture. Cells on these films showed typical multi- or bipolar elongated fibroblastic morphology with good spread.

Sponge. Fibroblast growth porous sponge material B (disulfide configuration) matched that of some of the better films. During the assay, cells were witnessed to attach to the upper surface of the sponge. By light microscopy, the morphological appearance of these cells was deemed similar on all substrates compared to the no-matrix control. Cells were observed by microscopy to infiltrate the sponge material.

Powder. A keratin powder dilution series was established and the result presented in the graph as material E. This result represents the observed growth curve for the concentration 2 $mgml^{-1}$. Higher concentration solutions than this resulted in the same curve, lower demonstrated a slightly higher cell proliferation rate than the control. Extract tests suggest the keratin powder itself may be, at sufficient concentration, mitogenic for sheep fibroblasts.

Figure 3:
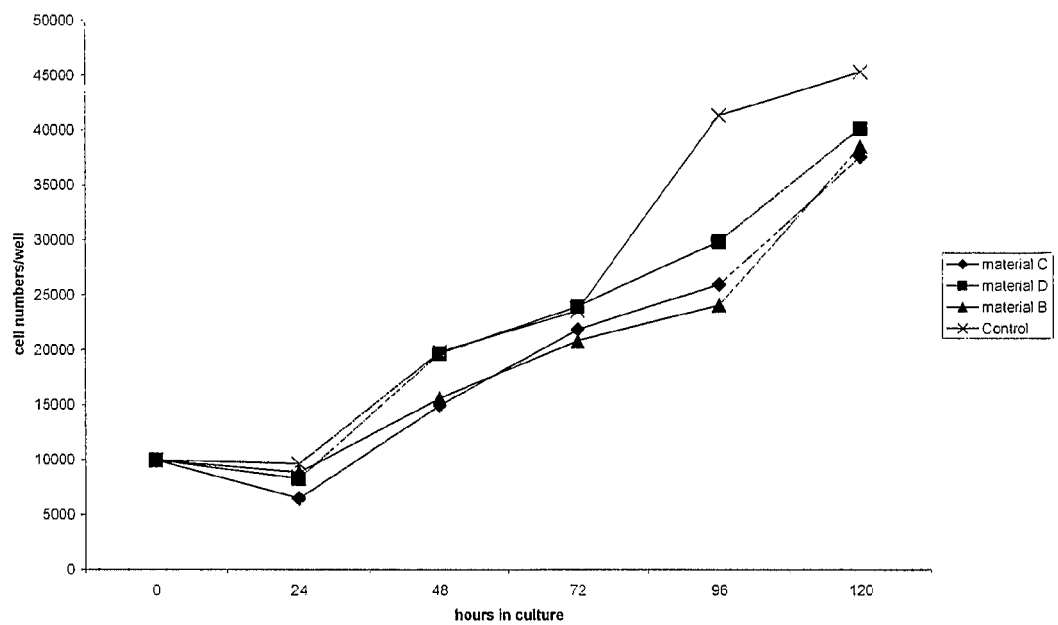
FIG. 3: shows human fibroblast proliferation on keratin materials.

Human Fibroblasts:

FIG. 3 is a graph showing the effect of different keratin matrices on human dermal fibroblast cell proliferation relative to cell media alone (control)

Human fibroblastic data for the corresponding keratin substrates more or less mirrored that observed with the sheep cell line. Again a typical growth curve was established over the 120 h period, however 100% confluence was reached in the control wells by the end of this time. At 120 h, cultures grown in the presence of the majority of test materials ranged from 83-89% confluence.

Sheep Lymphocytes

Figure 4:
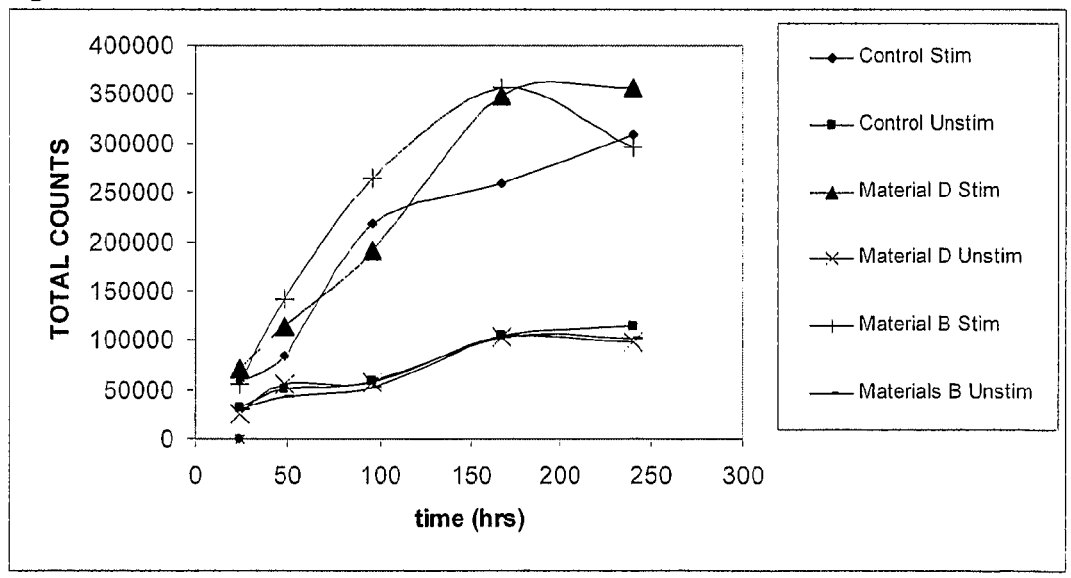
FIG. 4: shows the effect of Con(A) stimulation on T-cell growth in the presence of keratin matrices.

FIG. 4 demonstrates the effect of ConA stimulation on T cells grown in the presence/absence of keratin matrices over a 10-day period. Tritiated thymidine counts were converted to cell numbers per well (against a series of standards) for each of the treatment groups.

Resulting analysis suggests:
1. There is a marked difference in cell numbers over the 240 h experiment between ConA stimulated and non-activated sheep T lymphocyte cells. Control (grown in the absence of keratin biopolymers) cell numbers show a 6-fold difference between unstimulated and stimulated cells at 240 h. Cells grown in the absence of conA reached concentrations of 50000 cells/well at Day 10, whilst control cells with ConA supplementation exceeded 300000 cells/well at the same point. Such high concentrations were obtainable as the cells were maintained in suspension culture therefore reduced nutrient supply and not surface area requirement was the limiting factor.
2. There was little difference in cell proliferation rates between sample (matrix presence) and control (matrix absence) wells. This effect was noted for both stimulated cells and unstimulated cells. In other words:
   (a) Unstimulated cells grown in the presence of matrices proliferated at the same degree as those grown purely on tissue culture reference wells. This indicates that although the keratin biomaterials are not non-immunogenic, they look to be antigenically inert. If they were non-immunogenic, one would expect no proliferation of lymphocytes exposed to the biomaterial. If indeed it is inert, cell proliferation rates would mimic those of the control as appears the case.
   (b) Stimulated cells grown in the presence of the matrices proliferated at a similar rate or slightly higher than the control wells (which contained no keratin matrix). This suggests the activated T-cells are not being inhibited in any way by the matrix itself or any degradative by-products it may produce over this short time-course. Failure to inhibit active T-cells by the tested biomaterials demonstrates the product does not interfere with the normal cell-mediated immune response.

Figure 5:
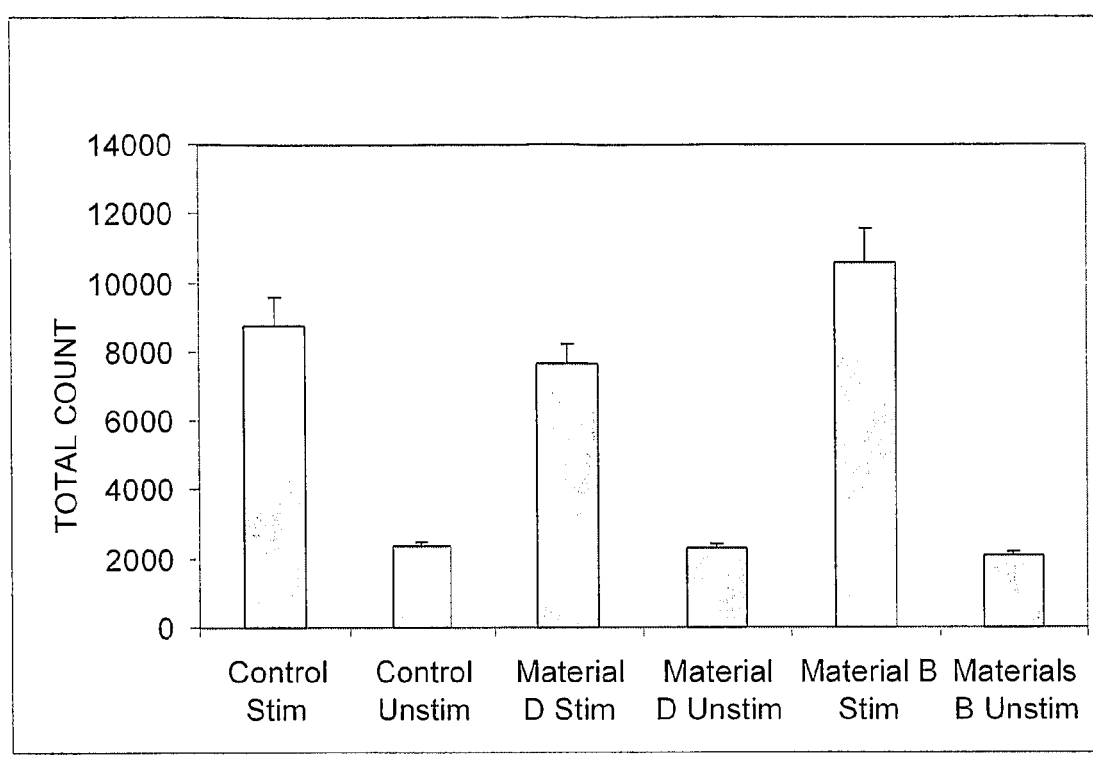
FIG. 5: shows the effect of Con(A) on stimulation of T-cell growth in the presence of keratin matrices after 72 hours.

FIG. 5 shows the effect of ConA stimulation on T-lymphocytes cells grown in the presence of a variety of matrices at 72 h. Total counts reflect the level of thymidine uptake and incorporation into DNA, which is then used as a measure of proliferation (see in the previous graph). A 72 h culture is regarded as the best measure of time for comparison between treatments as the cells are well within exponential phase growth.

The results are presented as a vertical bar graph with stimulated and non-stimulated treatments beside each other. Error bars represent means±SD for n=3. The unstimulated well counts (unlabelled) show very little variation with small error scores. Total counts for stimulated cells are slightly more variable although student T test analyses indicate only the material C is significantly different (p=0.075) from the control.

Unprimed T cells were shown to proliferate at the same degree in the presence or absence of the matrices. This showed the biomaterials were not non-immunogenic but instead inert. No single matrix tested stimulated the normal immune response to any degree greater than the control (no matrix well series).

Activated T cells maintained in culture with keratin matrices proliferated normally at a similar or greater than rate compared to those of the control (no matrix present). This demonstrates the biomaterials are biocompatible with stimulated T cells, mitogenic to a degree and most certainly do not interfere with the normal immune response. There was no inhibition of activated T cells by any matrix or its byproducts.

In summary, the tested matrices do not interfere with the body's cell-mediated immune response and are biocompatible with a sheep T lymphocyte cell line.

In vivo Testing

The effect of keratin matrices in a wound environment was determined using an animal model.

A randomised trial was conducted applying 4 samples to groups of rats with excision wounds. There were 6 male rats per group. Two wounds (8 mm diameter) were established on the back of each rat along the mid-line. One wound served as the control with the vehicle or saline was applied and the test material was applied to the other wound. The rate of healing was monitored by regular photographs. The wounds were photographed every second day and the area of the healing wounds were quantified. The percentage (%) change for each wound was determined at each time point and relative rate of healing of the experimental to the control wound determined for each rat. The mean difference at each time was then calculated and is detailed in table 4.

The dressings studied were: KP-U: Keratin membrane wound dressing (example 1), KP-T: Keratin membrane wound dressing (example 3), HG-GL: Keratin hydrogel (example 4), HG-O: Keratin hydrogel (example 2), HG-C commercially available hydrogel wound dressing product.

Twenty-four rats were used in the trial and trial studies were carried up to healing endpoint.

Results based on wound healing rate can be summarized as follows:
  i) the HG-GL wound dressing material significantly hastened the healing, with the most marked difference occurring in the early stages of healing.
  ii) the KP-T wound dressing material showed some improvement in healing rate, especially over the first 3 to 5 days.

TABLE 4

Area occupied by wound site following administration of various wound dressings. KP-U: Keratin membrane wound dressing (example 1), KP-T: Keratin membrane wound dressing (example 3), HG-GL: Keratin hydrogel (example 4). HG-O: Keratin hydrogel (example 2), HG-C commercially available hydrogel wound dressing product.

| Days after wound administration | Wound area, % of original | | | | | |
|---|---|---|---|---|---|---|
| | KP-U | KP-T | HG-O | HG-GL | HG-C | Blank |
| 1 | 100 | 100 | 100 | 100 | 100 | 100 |
| 3 | 102 | 90 | 97 | 77 | 97 | 93 |
| 5 | 94 | 90 | 81 | 70 | 90 | 84 |
| 9 | 64 | 69 | — | — | — | — |
| 11 | 39 | 33 | 35 | 24 | 40 | 36 |
| 13 | 28 | 24 | 23 | 13 | 25 | 23 |
| 15 | 15 | 11 | 19 | 9 | 13 | 18 |
| 17 | 18 | 11 | 14 | 5 | 6 | 12 |
| 19 | 5 | 3 | 8 | 2 | 2 | 6 |

EXAMPLES

The methods for the preparation of various forms of keratin are now described by way of example.

Example 1

Production of Keratin Membranes for Use in a Wound Care Product

A 10% S-sulfonated keratin intermediate filament protein (SIFP) solution was prepared using of S-sulfonated keratin intermediate filament protein powder dissolved in distilled water with gradual addition of 1M NaOH over 2 hours under mechanical stirring. The pH was maintained in the range 8.0-9.5, and finally adjusted to 8.5. The keratin protein solution was centrifuged at 27000 g for 10 mins in order to remove any air bubbles and undissolved material. The resulting keratin protein solution was cast into a petri dish and the solvents evaporated wider ambient conditions to leave a keratin membrane. The solvent can also include some percentage of organic based aqueous miscible solvent, such as an alcohol.

Example 2

Production of a Keratin Hydrogel for Use in Wound Care Products

A 10% S-sulfonated keratin intermediate filament protein (SIFP) solution was prepared as describe in Example 1. The solution was then intimately mixed with water soluble polymers such as polyvinyl alcohol (PVA) comprising 20% solid content and polyvinyl pyrrolidone (PVP) comprising 10% solid content to a achieve a optimum rheology and optimal composition i.e., SIFP:PVA:PVP=100:60:40 (w/w, %) for creating hydrogel. The combined solution was then cast, and hardened through a freezing-thawing cycle to produce a keratin based hydrogel. This involved freezing the material at −80° C. for 1 hr and thawing at 23° C. for 1 hour. This freeze-thaw cycle was repeated up to 7 times to obtain a hydrogel. The resulting hydrogel was washed with distilled water multiple times to remove any unreacted keratin and polymers.

Example 3

Production of Cross-Linked Keratin Membranes for Use in a Wound Care Product In order to improve the physical strength and also mechanical properties of materials produced as described in Example 1 membranes were treated with reductants to induce chemical cross-linking. Immersion of the membranes in a solution of 0.25M ammonium thioglycollate adjusted to pH 7.0 for 60 minutes was used to remove the sulfonate group from the S-sulfonated keratin protein (SIFP), and allow the formation of disulfide bonds (—S—S—). The resulting membranes were washed multiple times with distilled water to remove any residual reagents.

Example 4

Production of Chemical Cross-Linked Keratin Hydrogel for Use in a Wound Care Product Following preparation of the keratin, PVA, PVP solution as described in example 2, 0.05% to 0.1% of glutaraldehyde cross-linking agent was added into the blended solution. The combined solution was then cast, and hardened through a freezing-thawing cycle to produce a keratin based hydrogel. This involved freezing the material at −80° C. for 1 hr and thawing at 23° C. for 1 hour. This freeze-thaw cycle was repeated up to 7 times to obtain a hydrogel. The resulting hydrogel was washed with distilled water multiple times to remove any unreacted keratin and polymers, as well residues of unreacted glutaraldehyde. Physical observation showed significant improvement of their dimension stability or strength. These characteristics are also confirmed by the hydrogels insolubility behaviour in aqueous solvent, after having been made as an intimate blending keratin protein and polymers from an aqueous solvent (i.e., water).

Example 5

Production of Disulfide Cross-Linked Keratin Membrane for Use in a Wound Care Product A 10% S-sulfonated keratin intermediate filament protein (SIFP) solution was prepared as describe in Example 1. The solution was then intimately mixed with 1% of 0.25M ammonium thioglycollate solution ($NH_4TG$), where compositions are as: SIFP:$NH_4TG$=99:1 (w/w, %). The blended solution was then cast into a petri dish and the solvents evaporated under ambient conditions to create a disulfide cross-linked keratin membrane. The resulting membrane was washed with distilled water multiple times to remove any residual $NH_4TG$.

Example 6

Production of Disulfide Cross-Linked Keratin Hydrogel for Use in a Wound Care Product A 10% S-sulfonated keratin intermediate filament protein (SIFP) solution was prepared as describe in Example 1. The solution was then intimately mixed with 1% of 0.25M ammonium thioglycollate solution ($NH_4TG$), where compositions were: SIFP:$NH_4TG$=99:1 (w/w, %). The blended solution was then cast, and hardened through a freezing-thawing cycle to produce a disulfide cross-linked keratin hydrogel. This involved freezing the material at −80° C. for 1 hour and thawing at 23° C. for 1 hour. This freeze-thaw cycle was repeated up to 7 times to obtain a chemical cross-linked hydrogel.

Example 7

Production of an Uncrosslinked Keratin Hydrogel for Use in a Wound Care Product A 10% S-sulfonated keratin intermediate filament protein (SIFP) solution was prepared as describe in Example 1. The solution was cast, and hardened through a freezing-thawing cycle to produce a keratin based hydrogel. This involved freezing the material at −80° C. for 1 hour and thawing at 23° C. for 1 hour. This freeze-thaw cycle was repeated up to 7 times to obtain a keratin protein hydrogel.

INDUSTRIAL APPLICABILITY

The invention will be useful in a wide range of wound care products. Such products will assist in the healing and rate of healing of wounds by providing a biochemical environment around the wound site that induces healing.

The invention claimed is:

1. A wound care hydrogel comprising S-sulfonated keratin associated with a water soluble polymer through hydrogen bonding and further comprising a protein cross-linking agent.

2. The wound care hydrogel of claim 1 where the S-sulfonated keratin is S-sulfonated keratin intermediate filament protein, the water soluble polymer is selected from the group consisting of polyvinyl alcohol and polyvinyl pyrrolidone and mixtures thereof, and the protein crosslinking agent is selected from the group consisting of glutaraldehyde, formaldehyde, carbodiimide, 2,5-hexanedione, diimidate, bisacrylamide and mixtures thereof.

3. The wound care hydrogel of claim 2 where the protein crosslinking agent comprises glutaraldehyde.

4. A wound care hydrogel comprising S-sulfonated keratin associated with a water soluble polymer through hydrogen bonding.

5. The wound care hydrogel of claim 4 where the S-sulfonated keratin is S-sulfonated keratin intermediate filament protein and the water soluble polymer is selected from the group consisting of polyvinyl alcohol and polyvinyl pyrolidone and mixtures thereof.

6. A method for treating a wound comprising applying a wound site a wound care hydrogel according to claim 1.

7. A method for treating a wound comprising applying a wound site a wound care hydrogel according to claim 2.

8. A method for treating a wound comprising applying a wound site a wound care hydrogel according to claim 3.

9. A method for treating a wound comprising applying a wound site a wound care hydrogel according to claim 4.

10. A method for treating a wound comprising applying a wound site a wound care hydrogel according to claim 5.

* * * * *

UNITED STATES PATENT AND TRADEMARK OFFICE
CERTIFICATE OF CORRECTION

PATENT NO. : 7,732,574 B2
APPLICATION NO. : 10/583445
DATED : June 8, 2010
INVENTOR(S) : Robert James Kelly, Alisa Dawn Roddick-Lanzilotta and Mohammad Azam Ali Page 1 of 1

It is certified that error appears in the above-identified patent and that said Letters Patent is hereby corrected as shown below:

Column 13, line 11 of the claims, after "A method for treating a wound comprising applying" insert --to--.

Column 14, line 1 of the claims, after "A method for treating a wound comprising applying" insert --to--.

Column 14, line 3 of the claims, after "A method for treating a wound comprising applying" insert --to--.

Column 14, line 5 of the claims, after "A method for treating a wound comprising applying" insert --to--.

Column 14, line 7 of the claims, after "A method for treating a wound comprising applying" insert --to--.

Signed and Sealed this

Fourteenth Day of September, 2010

David J. Kappos
*Director of the United States Patent and Trademark Office*